United States Patent
Kohama

(10) Patent No.: US 6,518,582 B1
(45) Date of Patent: Feb. 11, 2003

(54) ELECTRON BEAM APPARATUS, AND INSPECTION INSTRUMENT AND INSPECTION PROCESS THEREOF

(75) Inventor: Yoshiaki Kohama, Kawasaki (JP)

(73) Assignee: Nikon Corporation, Tokyo (JP)

( * ) Notice: Subject to any disclaimer, the term of this patent is extended or adjusted under 35 U.S.C. 154(b) by 27 days.

(21) Appl. No.: 09/664,136

(22) Filed: Sep. 19, 2000

(30) Foreign Application Priority Data

Sep. 21, 1999 (JP) .......................................... 11-267402

(51) Int. Cl.[7] ........................ G01N 23/00; H01J 37/244
(52) U.S. Cl. ..................... 250/492.2; 250/397; 250/310
(58) Field of Search .......................... 250/492.2, 492.22, 250/397, 398, 310

(56) References Cited

U.S. PATENT DOCUMENTS

| | | | | |
|---|---|---|---|---|
| 3,916,204 A | * | 10/1975 | Swartz | 250/453.11 |
| 5,182,454 A | * | 1/1993 | Matsuda et al. | 250/310 |
| 5,933,217 A | * | 8/1999 | Nakasuji et al. | 250/492.2 |
| 5,955,738 A | * | 9/1999 | Manabe et al. | 250/492.22 |

FOREIGN PATENT DOCUMENTS

| | | |
|---|---|---|
| JP | 7-249393 | 9/1995 |
| JP | 10-197462 | 7/1998 |
| JP | 10-294345 | 11/1998 |

* cited by examiner

Primary Examiner—Bruce Anderson
(74) Attorney, Agent, or Firm—Oliff & Berridge PLC

(57) ABSTRACT

An electron beam apparatus prevents a rapid increase of dosage caused by stoppage or deceleration of movement and protects the specimen when the specimen is irradiated with the electron beam while the specimen and the electron beam are being relatively moved. An electron beam source outputs the electron beam. The dosage of electron beam irradiated per unit area of the specimen is measured. A storage section stores a predetermined dosage per unit area in memory for the specimen. A detector detects over exposure of the electron beam when the measured dosage per unit area is greater than the dosage per unit area stored in the storage section. A controller controls the electron beam source to reduce the dosage per unit area of the electron beam lower than the dosage per unit area stored in the storage section.

17 Claims, 13 Drawing Sheets

ELECTRON BEAM APPARATUS, AND INSPECTION INSTRUMENT AND INSPECTION PROCESS THEREOF

BACKGROUND OF THE INVENTION

1. Field of Invention

The present invention relates to an electron beam apparatus for irradiating a specimen to be inspected with an electron beam, and an inspection apparatus and inspection method for inspecting the specimen by the use of this electron beam apparatus.

2. Related Background Art

As is generally known, an electron beam apparatus for irradiating the specimen with an electron beam is equipped with an electron gun and electron optical system (electron lenses, etc.). In the electron beam apparatus, the electron beam discharged from the electron gun is applied on the specimen surface via the electron-optical system.

For an example of the equipment incorporating this electron beam apparatus, a description will be made on a scanning electron microscope (SEM) and electron beam inspection apparatus (EB inspection apparatus). By the way, to the SEM and EB inspection apparatus, a mechanism for detecting secondary electrons generated from the specimen by irradiating a specimen with an electron beam and creating a specimen image is incorporated.

To acquire the specimen image in SEM, the specimen is held stationary and the specimen surface is two-dimensionally scanned with the electron beam squeezed in the form of spot (spot beam). Consequently, SEM is popularly used for observing a comparatively small region (defect portion, etc.) of the specimen surface. The inspection of the whole specimen surface by SEM is not realistic do to its low throughput.

As against this, the EB inspection apparatus has been under development in recent years in order to satisfy the requirements of inspecting a comparatively wide area or the whole area of the specimen surface.

For example, in the Japanese Patent Application Laid-Open (JP-A) No. 7-249393 or in the Japanese Patent Application Laid-Open (JP-A) No. 10-197462, there are disclosed EB inspection apparatus in which by scanning the specimen surface with the electron beam shaped in the form of a rectangle (rectangle beam) while the stage is being continuously moved, the specimen image is obtained.

In addition, in the Japanese Patent Application Laid-Open (JP-A) No. 10-294345, there is disclosed an EB inspection apparatus which acquires the specimen image by continuously moving the stage in one direction and allowing the spot beam to scan the specimen surface in the direction crossing at right angles the one direction mentioned above.

In these EB inspection apparatus, since the specimen image is acquired while the stage is being moved, the specimen image is able to be taken in continuously from a comparatively wide area or the whole area of the specimen surface. Consequently, the EB inspection apparatus is able to inspect the specimen surface at an incomparably higher speed than that of the whole surface inspection by SEM.

In addition, in the above-mentioned EB inspection apparatus, the inspection speed is able to be increased as much as the stage moving speed is increased.

SUMMARY OF THE INVENTION

Now, in the conventional EB inspection apparatus mentioned above, simply increasing the stage moving speed lowers the total current volume of electron beam irradiated over the specimen (hereinafter called the "dosage") and the specimen image is degraded. In order to prevent this image degradation, the current volume of the electron beam discharged from the electron gun must be increased as much as the stage moving speed is increased. In this way, the high-speed inspection in the conventional EB inspection apparatus has been carried out by continuously irradiating the specimen surface with the large-current electron beam while the stage is being continuously moved at a high speed.

However, even during the high-speed inspection, the stage may be stopped or the moving speed may be decreased for some reason. If this kind of stage stop or speed reduction should occur during the high-speed inspection, the large-current electron beam continued to strike against the same place or the vicinity of the specimen surface, and the dosage rapidly increases at the relevant place.

On the other hand, there is a limit of acceptable dosage for the specimen, and if the electron beam continues to be irradiated to the level exceeding the allowable range of the dosage, contamination or charge-up occurs in the specimen, or for the worst, the specimen may be destroyed.

This kind of problem occurs even when the scanning by the spot beam is stopped or decelerated in the EB inspection apparatus disclosed in the Japanese Patent Application Laid-Open (JP-A) No. 10-294345.

It is an object of the present invention to provide an electron beam apparatus, inspection apparatus, and inspection method that can prevent a rapid increase of dosage caused by stop or deceleration of the relative move and can protect the specimen when the specimen is irradiated with the electron beam while the specimen and the electron beam are being relatively moved.

An electron beam apparatus according to the present invention is an electron beam apparatus for irradiating a specimen to be inspected with the electron beam comprising an electron beam outputting means for outputting the electron beam, a measuring means for measuring the dosage of electron beam irradiated per unit area of the specimen, a storage section for storing the predetermined dosage per unit area for the specimen, a detection means for detecting over exposure of the electron beam when the dosage per unit area measured by the measuring means is greater than the dosage per unit area stored in the storage section, and a control means for controlling the electron beam outputting means to reduce the dosage per unit area of the electron beam than the dosage per unit area stored in the storage section, when the over exposure of electron beam is detected by the detection means.

When the dosage of electron beam irradiated per unit area of the specimen is measured by the measuring means and the measured dosage is detected to be larger than the dosage stored in advance in the storage section in this way, the electron beam outputting means is controlled to reduce the dosage than that stored in the storage section. By this, when the specimen is irradiated with the electron beam while the electron beam irradiating position and the specimen position are relatively moved, the dosage of the electron beam to be applied to the specimen is able to be held to a predetermined dosage range stored in the storage section.

In addition, in the electron beam apparatus, the control means desirably controls to make the dosage of electron beam per unit area smaller than the dosage per unit area stored in the storage section when the over exposure of electron beam is detected over a specified time.

In the electron beam apparatus, the control means controls the electron beam outputting means in such a manner to make the dosage per unit area of the electron beam applied to the specimen smaller than the dosage per unit area stored in the storage section by expanding the irradiation range of the electron beam.

Furthermore, the electron beam apparatus may further comprise a stage for placing the specimen and a moving means for moving the stage, and may be characterized in that the measuring means measures the dosage per unit area in accordance with the output current volume of electron beam and the moving speed of the stage moved by the moving means.

Because the irradiation current volume of the electron beam applied to the specimen placed on a stage has a specified relation with the output current volume of the electron beam, the dosage per unit area is able to be measured in accordance with the output current volume of the electron beam and the stage moving speed.

In the electron beam apparatus, the measuring means may be measure the dosage per unit area in accordance with the secondary beam volume generated from the specimen.

Because the volume of the secondary beam generated from the specimen is defined in accordance with the volume of the electron beam impinging on the specimen, the dosage is able to be measured by the volume of the secondary beam.

The electron beam apparatus according to the present invention comprises an electron beam output means for outputting the electron beam, a stage irradiated with the electron beam outputted by the electron beam outputting means, a moving means for moving the stage, a storage section for storing the stage moving speed predetermined in accordance with the specimen and the output current volume of the electron beam, a detection means for detecting over exposure of the electron beam when the moving speed of the stage moved by the moving means is smaller than the moving speed stored in the storage section, and a control means for controlling the electron beam outputting means to prevent the stage from being irradiated with the electron beam when the over exposure of electron beam is detected by the detection means.

In this way, when the stage moving speed by the moving means is compared with the predetermined moving speed stored in the storage section and if the actual stage moving speed is smaller than the moving speed stored in the storage section, the over exposure of electron beam is detected. And when the over exposure of electron beam is detected, the control means controls the electron beam not to be applied to the stage, thereby quickly detecting the over exposure of the electron beam and stopping the electron beam from being irradiated over the stage.

The electron beam apparatus according to the present invention is an electron beam apparatus for irradiating the specimen to be inspected with the electron beam, and comprises an electron beam outputting means for outputting the electron beam, a storage section for storing the output current volume of the electron beam and the volume of the secondary beam predetermined in accordance with the specimen and the output current volume of the electron beam, a detection means for detecting the over exposure of the electron beam when the volume of the secondary beam generated from the specimen is greater than the volume of the secondary beam stored in the storage section, and a control means for controlling the electron beam outputting means to prevent the stage from being irradiated with the electron beam when the over exposure of the electron beam is detected by the detection means.

The volume of the secondary beam generated from the specimen in this way is compared with the volume of the secondary beam stored in the storage section, and when the volume of the generated secondary beam is greater than the volume of the secondary beam stored in the storage section, the over exposure of the electron beam is detected. And when the over exposure of the electron beam is detected, the control means controls the electron beam from being applied to the stage, thereby quickly detecting the over exposure of the electron beam and preventing the electron beam from being applied to the stage.

The inspection apparatus according to the present invention comprises the electron beam apparatus and an image acquisition means for acquiring the image information of the specimen in accordance with the secondary beam generated from the specimen.

By configuring an inspection apparatus equipped with an electron beam apparatus, it is possible to prevent the condition in which the specimen to be inspected is destroyed by over exposure of the electron beam.

In addition, in the inspection apparatus, the measuring means may be intended to measure the dosage on the basis of the output current volume of the electron beam and the contrast ratio of the image information acquired by the image acquisition means.

Because the contrast ratio of the image information formed on the basis of the secondary beam is determined by the dosage of the electron beam impinged in the specimen, the dosage can be measured by the contrast ratio of the image information.

In addition, the inspection apparatus according to the present invention is an inspection apparatus for inspecting the specimen by irradiating the specimen to be inspected with the electron beam, comprises an electron beam outputting means for outputting the electron beam and irradiating the specimen with the electron beam, a storage section for storing the contrast ratio predetermined on the basis of the specimen and the output current volume of the electron beam, a detection means for detecting the over exposure of the electron beam when the contrast ratio of the image information acquired by the image acquisition means is greater than the contrast ratio stored in the storage section, and a control means for controlling the electron beam outputting means to prevent the electron beam from being applied to the specimen.

In this way, the contrast ratio of the image information based on the secondary beam generated from the specimen is compared with the contrast ratio of the image information predetermined and stored in the storage section, and when the contrast ratio of the image information based on the secondary beam actually generated is greater than the contrast ratio of the image information stored in the storage section, the over exposure of the electron beam is detected. And when the over exposure of the electron beam is detected, the control means controls the electron beam from being applied to the specimen to quickly detect the over exposure of the electron beam and stops electron beam from being applied to the specimen.

The inspection method according to the present invention is an inspection method for inspecting the specimen by irradiating the specimen to be inspected with the electron beam and comprises an electron beam irradiation step for outputting the electron beam and irradiating the specimen with the electron beam, an image acquisition step for acquiring the image information of the specimen based on the secondary beam generated from the specimen, a measuring step for measuring the dosage of the electron beam irradiated per unit area of the specimen, a detection step for detecting the over exposure of the electron beam when the dosage per unit area measured in the measuring step is greater than the dosage per unit area predetermined for the specimen, and a control step for controlling the electron beam outputting means in such a manner that the dosage per unit area of the electron beam is made smaller than the dosage per unit area stored in the storage section when the over exposure of the electron beam is detected in the detection step.

The dosage of the electron beam irradiated per unit area of the specimen is measured in this way, and the measured dosage and the dosage stored in the storage section predetermined are compared to detect the over exposure of the electron beam. And because the dosage is brought to be reduced when the over exposure of the electron beam is detected, it is possible to prevent the condition in which the specimen to be inspected is not destroyed by the electron beam.

The inspection method according to the present invention is an inspection method for inspecting the specimen by irradiating the specimen to be inspected with the electron beam, and comprises an electron beam irradiating step for outputting the electron beam to irradiate the specimen with the electron beam, an image acquisition step for acquiring the image information of the specimen based on the secondary beam generated from the specimen, a stage moving step for moving the stage with the specimen placed, and a detection step for detecting the over exposure of the electron beam when the moving speed of the stage moved in the stage moving step is smaller than the stage moving speed predetermined in accordance with the specimen and the output current volume of the electron beam, and a control step for controlling the electron beam to prevent the stage from being irradiated with the electron beam when the stage is detected to be overexposed with the electron beam in the detection step.

In this way, when the stage moving speed is compared with the moving speed predetermined and stored in the storage section and the moving speed of the actual stage is smaller than the moving speed stored in the storage section, the over exposure of the electron beam is detected. And when the over exposure of the electron beam is detected, control is made to prevent the stage from being irradiated with the electron beam in the control step. With this contrivance, the over exposure of the electron beam is quickly detected and it is able to stop the stage from being irradiated with the electron beam.

The present invention will be more fully understood from the detailed description given hereinbelow and the accompanying drawings, which are given by way of illustration only and are not to be considered as limiting the present invention.

Further scope of the applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will be apparent to those skilled in the art from this detailed description.

DESCRIPTION OF THE PREFERRED EMBODIMENTS

Figure 1:
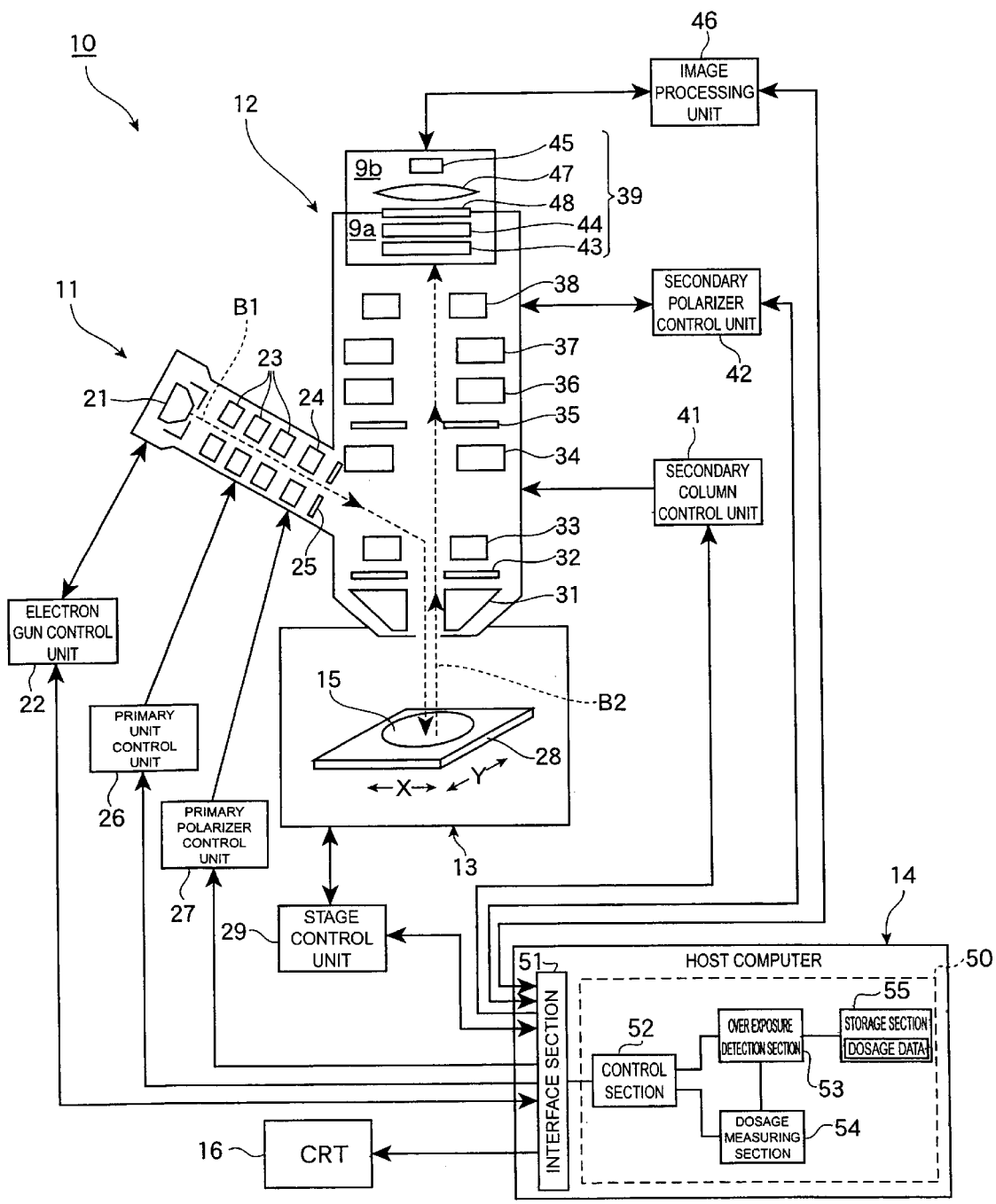
FIG. 1 is a drawing showing the overall configuration of the EB inspection apparatus 10 according to the present embodiment.

Referring now to the drawings, preferable embodiments according to the present invention will be described in detail hereinafter. In explaining the drawings, the like reference characters are assigned to like or corresponding parts throughout, and redundant explanation will be omitted.

FIG. 1 is a drawing showing the EB inspection apparatus 10 that incorporates the electron beam apparatus according to the present embodiment. The EB inspection apparatus 10 has a capability to acquire the image of the specimen placed on the stage 28, and it is able to change over the operation mode for acquiring the specimen image with the stage 28 stopped (hereinafter called the "observation mode") to the operation mode for acquiring the specimen image at a high speed with the step 28 moved (hereinafter called the "inspection mode"). The EB inspection apparatus 10 is characterized in a mechanism 50 incorporated for protecting the specimen on the stage 28 (hereinafter called the "specimen protection mechanism") when the operation in the inspection mode becomes a condition in which the specimen is irradiated with the electron beam in excess for some reason. The specimen protection mechanism 50 will be described later.

The EB inspection apparatus 10 is equipped with the primary column 11, secondary column 12, and the chamber 13 as illustrated in FIG. 1. The primary column 11 is mounted aslant to the side surface of the secondary column 12. To the lower part of the secondary column 12, the chamber 13 is installed. These primary column 11, secondary column 12, and chamber 13 are evacuated by a turbo pump of the vacuum evacuation system not illustrated, and the vacuum condition inside is maintained.

Now, the description will be made on the configuration of the primary column 11, secondary column 12, and chamber 13, respectively.

Inside the primary column 11, an electron gun 21 is arranged. The electron gun 21 accelerates and converges the thermion discharged from the cathode, and releases the electron beam. For the cathode of the electron gun 21, lanthanum hexaborite (LaB6) that is generally a rectangle cathode and can take out a large current is used. To the electron gun 21, an electron gun control unit 22 for controlling the acceleration voltage Vac of the electron gun 21 and on-off controlling the power supply of the electron gun 21 are connected. Furthermore, a gun alignment mechanism or gun aligner not illustrated for adjusting the position of the electron gun 21 are also mounted.

Figure 2:
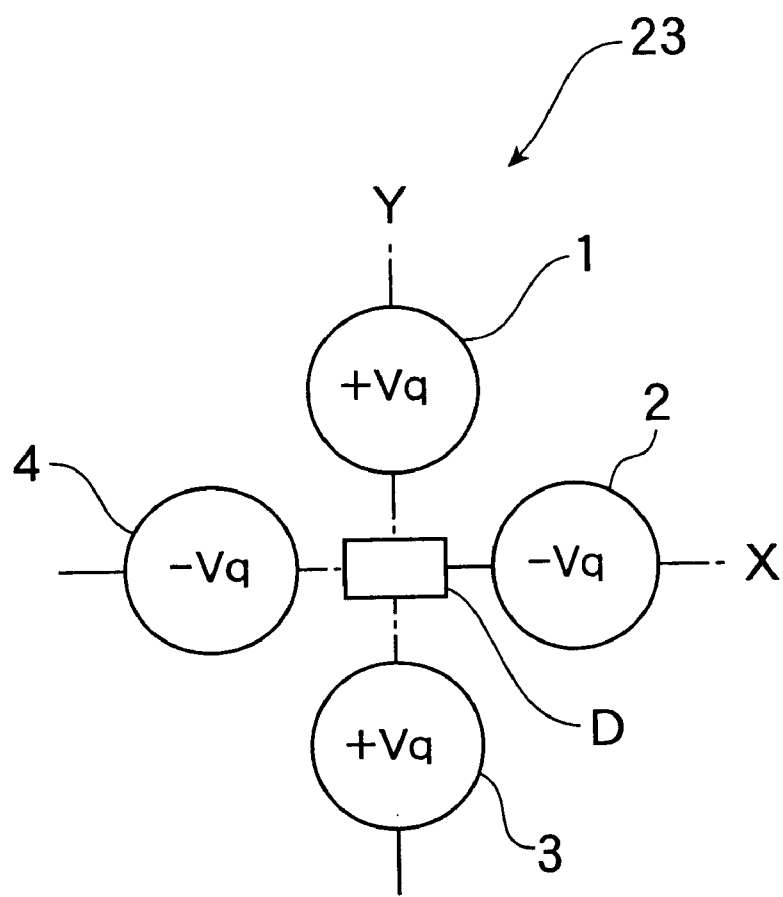
FIG. 2 is a drawing showing the configuration of the primary optical system 23.

On the optical axis of the electron beam discharged from the electron gun 21 (hereinafter called the "primary beam B1"), the primary optical system 23 formed in three stages, a primary polarizer 24, and an aperture 25 are arranged. Each stage of the primary optical system 23 consists of electrostatic quadrupole (or octupole) lenses (or electromagnetic lenses) of asymmetry rotation axis. For example, in the case of the electrostatic lens in which each of the primary optical system 23 consists of four cylindrical rods 1–4 as shown in FIG. 2, the cylindrical rods which are opposite to each other (1 and 3, 2 and 4) are set to the equivalent potential, and are provided with opposite voltage characteristics (+Vg to 1 and 3, −Vq to 2 and 4). With this configuration, same as the so-called cylindrical lens, the primary beam B1 is able to be focused or diverged. Consequently, according to this primary optical system 23, the lens voltage of each electrostatic lens is optimized and the cross section D of the primary beam B1 is able to be shaped into an optical form (rectangular or elliptical) without losing the discharged electrons. FIG. 2 shows the case in which the cross section of the primary beam B1 is rectangle. The lens voltage of each stage of the primary optical system 23 is controlled by the primary column control unit 26 (see FIG. 1) connected to the primary optical system 23.

Figure 3:
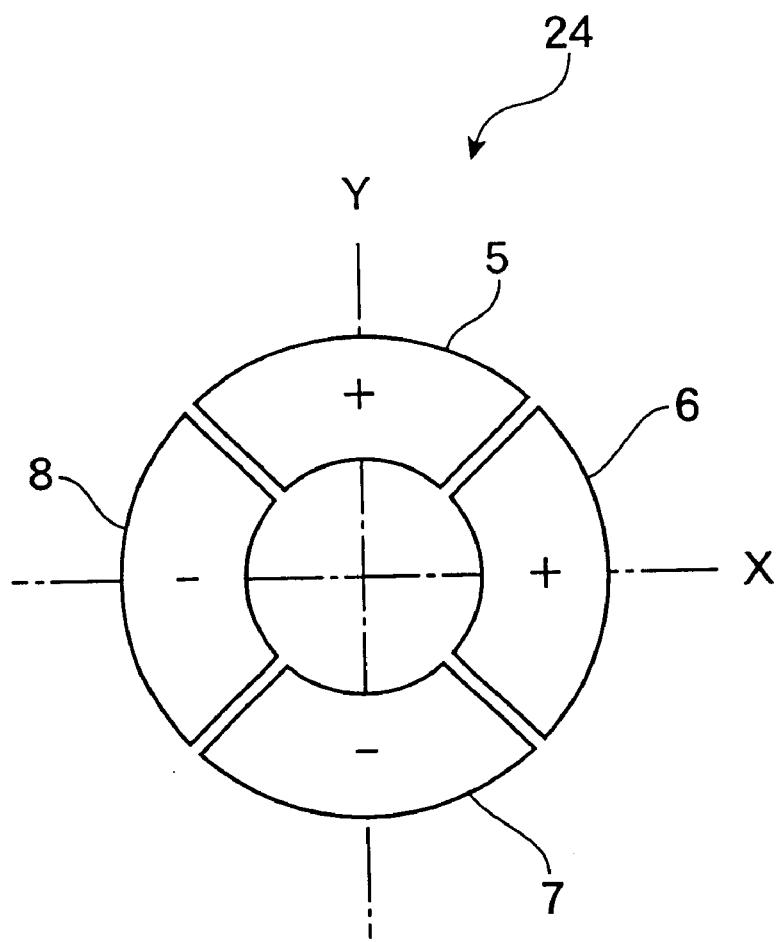
FIG. 3 is a drawing showing the configuration of the primary polarizer 24 and the secondary polarizer 38.

The primary polarizer 24 is formed by a electrostatic polarizer or electromagnetic polarizer. For example, when the primary polarizer 24 is an electrostatic polarizer consisting of four independent electrodes 5 to 8 as shown in FIG. 3, varying the voltage applied to the electrodes 6, 8 which are located opposite to each other along the X-axis can deviate the trajectory of the primary beam B1 in the X direction. In addition, varying the voltage applied to the electrodes 5, 7 which are located opposite to each other along the Y-axis can deviate the trajectory of the primary beam B1 in the Y direction. The voltage applied to each electrode of the primary polarizer 24 is controlled by the primary polarizer control unit 27 connected to the primary polarizer 24.

The electron gun control unit 22, primary column control unit 26, and primary polarizer control unit 27 are connected to the host computer 14.

Now, the description will be made on the chamber 13. Inside the chamber 13, a stage 28 on which the specimen 15 is placed and at the same time which is movable to X and Y directions is installed. To the stage 28, the specified retarding voltage Vr (later discussed) is applied. To the stage 28, a stage control unit 29 is connected. The stage control unit 29 drives the stage 28 in the X and Y directions and at the same time, reads the X, Y position of the stage 28 by the use of a laser interferometer (the data rate is, for example, 10 Hz), and outputs the XY position signal to the host computer 14. The stage control unit 29 detects the moving speed of the stage 28 based on the XY positions read and outputs the speed signal to the host computer 14.

Next description will be made on the secondary column 12. Inside the secondary column 12, a cathode lens 31, numerical aperture 32, Wien filter 33, second lens 34, field aperture 35, third lens 36, fourth lens 37, secondary polarizer 38, and detector 39 are arranged on the optical axis of the secondary beam B2 (later discussed) generated from the specimen 15.

Figure 4:
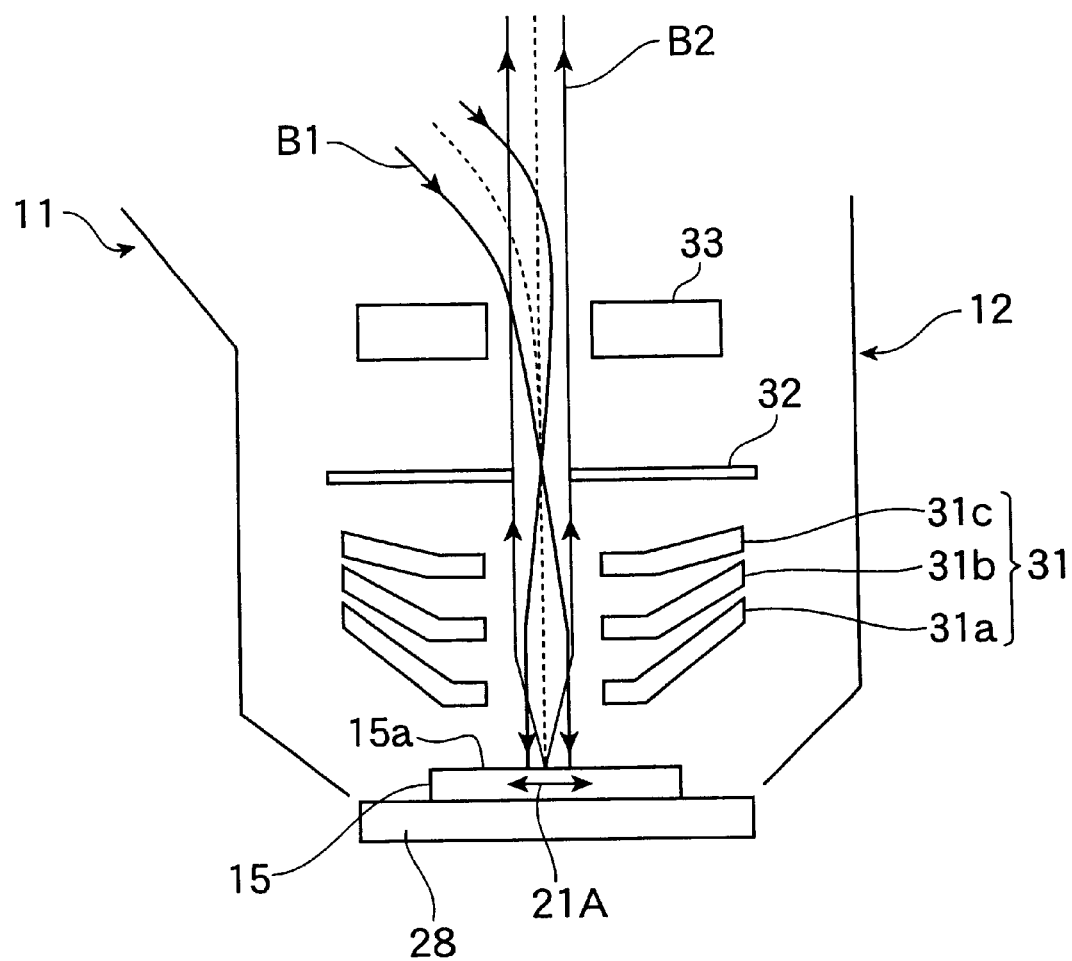
FIG. 4 is a drawing showing trajectories of the primary beam and the secondary beam.

The cathode lens 31 consists of three electrodes 31a, 31b, 31c as shown, for example, in FIG. 4. In this event, to the first electrode 31a and the second electrode 31b from below the cathode lens 31 (on the specimen 15 side), a specified voltage is applied, and the third electrode 31c is set to a zero potential.

The numerical aperture 32 corresponds to the opening throttle, and determines the opening angle of the cathode lens 31. The numerical aperture 32 is a thin film plate made of metal (Mo, etc.) with a round opening section formed, and the opening section is arranged to become a focus position of the cathode lens 31. Consequently, the numerical aperture 32 and the cathode lens 31 form a telecentric electron optical system. The numerical aperture 32 plays a function to impede the unwanted electrode beam that scatters in the EB inspection apparatus 10 from reaching the specimen 15 in order to prevent contamination of the specimen 15. In addition, the numerical aperture 32 plays a role to suppress the lens aberration of the second lens 34 to fourth lens 37 on the latter stages for the secondary beam B2 (later discussed).

The Wien filter 33 is a polarizer that works as an electromagnetic prism, which is capable for allowing the charged particle (for example, secondary beam B2) only that satisfies the Wien condition (E=vB, where v denotes the velocity of the charged particle, E the electric field, B the magnetic field, and E⊥B) to go straight and bending the trajectories of other charged particles (for example, primary beam B1).

The second lens 34, third lens 36, and fourth lens 37 are all symmetrical rotation axis type lenses called unipotential electrostatic lenses or Einzel lens, and consist of three electrodes, respectively. Each lens generally controls the lens actions by holding the two electrodes on the outside to a zero potential and varying the voltage applied to the center electrode sandwiched in between two electrodes.

The field aperture 35 is disposed between the second lens 34 and the third lens 36, and restricts the field of view to a required range as in the case of the field stop of the optical microscope. The field aperture 35 intercepts the unwanted secondary beam B2 together with the third lens 36 and the fourth lens 37 on the latter stage and prevents charge-up and contamination of the detector 39.

Each voltage of the cathode lens 31, second lens 34, third lens 36, and fourth lens 37 as well as the electromagnetic field applied to the Wien filter 33 are controlled by the secondary column control unit 41 connected to the secondary column 12.

The secondary polarizer 38 is a biaxially polarizable electrostatic polarizer comprising four independent electrodes 5 to 8 as with the primary polarizer 24 (see FIG. 3) described above. In this case, varying the voltage applied to electrodes 6, 8 can deviate the trajectory of the secondary beam B2 in the X direction. In addition, varying the voltage applied to electrodes 5, 7 can deviate the trajectory of the secondary beam B2 in the Y direction. The voltage applied to each electrode of the secondary polarizer 38 is controlled by the secondary polarizer control unit 42 connected to the secondary polarizer 38.

The detector 39 comprises an MCP (micro channel plate) 43 for accelerating and multiplying electrons, a fluorescent plate 44 for converting an electron image to an optical image, and TDI (time delay and integration) array CCD sensor (hereinafter called the "TDI sensor") 45 for picking up the optical image. Between the fluorescent plate 44 and the TDI sensor 45, an optical relay lens 47 is installed, which contracts the optical image on the fluorescent plate 44 to about ⅓ and projects on the image pick-up surface of the TDI sensor 45.

Between the fluorescent plate 44 and the optical relay lens 47, a view port 48 is disposed as a transmission window for transmitting the optical image. With this view port 48, the inside of the detector 39 is divided into a vacuum chamber 9a and an atmospheric chamber 9b.

Now, the image pick-up surface of the TDI sensor 45 comprises a plurality of light-receiving pixels arranged two-dimensionally. To the TDI sensor 45, an image processing unit 46 is connected. The secondary polarizer control unit 42, secondary column control unit 41, and image processing unit 46 are connected to the host computer 14. To the host computer 14, CRT 16 is connected.

Next discussion will be made on the host computer 14 connected to each control unit. The host computer 14 comprises a control section 52 for controlling each control unit and the interface section 51 for connecting the control section 52 to each control unit. The control section 52 is also capable for acquiring control information from each control unit. In addition, the host computer 14 has an dosage measuring section 54 for measuring the dosage applied to the specimen in conformity to the control information, a storage section 55 for storing the dosage prescribed for each specimen in memory, and an over exposure detection section 53 for detecting the over exposure of electron beam on the basis of the dosage measured by the dosage measuring section 54 and the dosage stored in the storage section 55. The specimen protection mechanism 50 comprises a control section 52 that is possessed by the host computer 14, a dosage measuring section 54, storage section 55, and over exposure detection section 53.

Now, the trajectory, etc. of the primary beam B1 and the secondary beam B2 in the EB inspection apparatus 10 (see FIG. 1) according to the present embodiment will be explained successively.

The primary beam B1 is discharged in a current volume corresponding to the acceleration voltage Vac of the electron gun 21. Now, the current volume of the primary beam B1 discharged from the electron gun 21 is hereinafter called the "outgoing current volume Ia." The primary beam B1 from the electron gun 21 passes and reaches the primary polarizer 24 while being subject to the lens actions of the primary optical system 23. When no voltage is applied to electrodes 5 to 8 (see FIG. 3) of the primary polarizer, the polarizing action of the primary polarizer 24 does not reach the primary beam B1, and the primary beam B1 passes the primary polarizer 24 and the aperture 25 successively and impinges aslant on the center section of Wien filter 33.

The primary beam B1 incident on the Wien filter 33 has the trajectory bent by the polarizing action of the Wien filter 33, and reaches the opening section of the numerical aperture 32. At this place, the primary beam B1 forms image at the opening section of the numerical aperture by the setting of the lens voltage of the primary optical system 23 (see FIG. 4). The specimen surface 15a is irradiated with the primary beam B1 which formed image at the opening section of the numerical aperture 32 via the cathode lens 31.

Since the numerical aperture 32 and the cathode lens 31 compose a telecentric electron optical system, as described above, the primary beam B1 that has passed the cathode lens 31 becomes a parallel beam. As a result, the primary beam B1 is applied perpendicularly and uniformly to the specimen surface 15a. That is, the Kohler illumination of the optical microscope is achieved.

To the stage 28 on which the specimen 15 is placed, the retarding voltage Vr is applied, and between the electrode 31a of the cathode lens 31 and the specimen 15, a electric field negative to the primary beam B1 is formed. Consequently, the primary beam B1 that has passed the cathode lens 31 is decelerated before it reaches the specimen surface 15a.

Now, the current volume of the primary beam B1 applied to the specimen surface 15a (hereinafter called the "irradiated current volume Ib") is far reduced as compared with the outgoing current volume Ia. Here, because the corresponding relation between the irradiated current volume Ib and the outgoing current volume Ia is known, and the corresponding relation between the outgoing current volume Ia and the acceleration voltage Vac of the electron gun 21 is known, the corresponding relation between the irradiated current volume Ib and the acceleration voltage Vac becomes known. Consequently, in the electron gun control unit 22, the irradiated current volume Ib of the primary beam B1 is able to be set to a required value by controlling the acceleration voltage Vac of the electron gun 21. The information concerning the setting of the irradiated current volume Ib is outputted from the electron gun control unit 22 to the host computer 14.

By the way, the irradiated current volume Ib is set to different values at the time of observation mode later discussed and at the inspection mode, as shown in Table 1.

TABLE 1

|  | OBSERVATION MODE | INSPECTION MODE |
|---|---|---|
| IRRADIATED CURRENT VOLUME IB OF PRIMARY BEAM (NA) | 62.5 | 250 |

Figure 5:
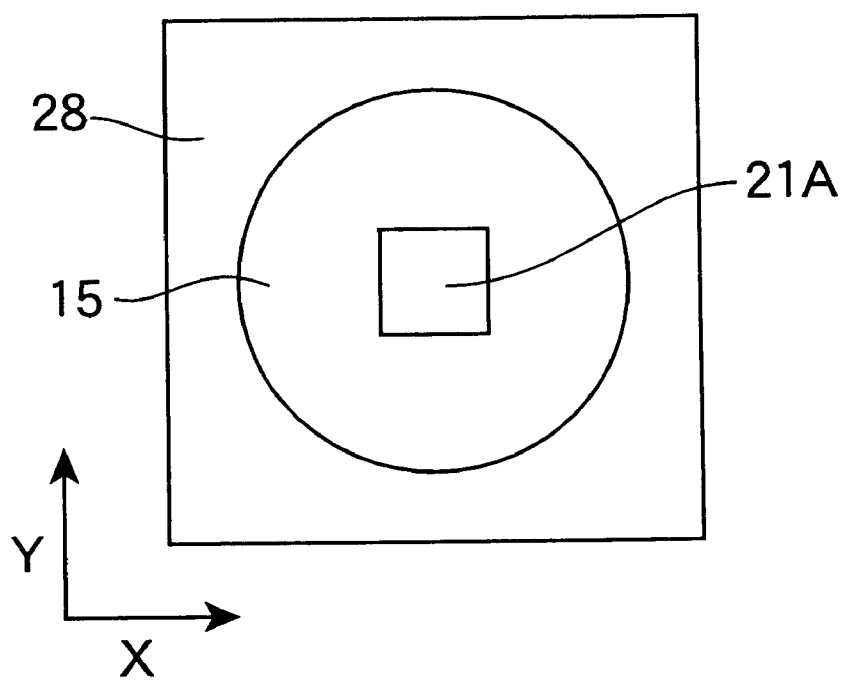
FIG. 5 is a drawing explaining the irradiation region 21A of the primary beam.

On the other hand, the profile of the irradiated region 21A (see FIG. 4) of the primary beam B1 in the specimen surface 15a is shaped into an optional profile (rectangular or elliptical) by controlling the lens voltage of the primary optical system 23. FIG. 5 shows an example when the irradiated region 21A is rectangular. In this way, in the EB inspection apparatus 10 according to the present embodiment, the specimen 15 located inside the rectangular irradiated region 21A is uniformly irradiated with the irradiated current volume Ib by the use of the primary beam B1 adjusted as described above.

Now, the dosage Do when the stage 28 is stopped (for example, in the observation mode) is given by the following equation (1) assuming that S denotes the area of the irradiated region 21A and T denotes the irradiation time of the primary beam B1. That is, the dosage Do increases in proportion to the irradiated current volume Ib and the irradiation time T.

$$Do = Ib \times T / S \tag{1}$$

The dosage Dv when the stage 28 is being moved (for example, in the inspection mode) is given by the following equation (2) when the moving speed V (≠0) of the stage 28 used. That is, the dosage Dv increases in inverse proportion to the moving velocity V of the stage.

$$Dv\ Ib \times V/S \qquad (2)$$

However, for the specimen 15, there is a limit of dosage which the specimen 15 can accept, and if the primary beam B1 is irradiated exceeding this allowable range of dosage, contamination or charge-up occurs in the specimen 15 or for the worst, the specimen 15 may be destroyed.

Consequently, the data concerning the allowable dosage range of the specimen 15 is predetermined for kinds of the specimen 15 and stored in memory in the storage section 55 of the host computer 14. The data concerning the allowable range of this dosage is utilized by the specimen protection mechanism 50.

Figure 6:
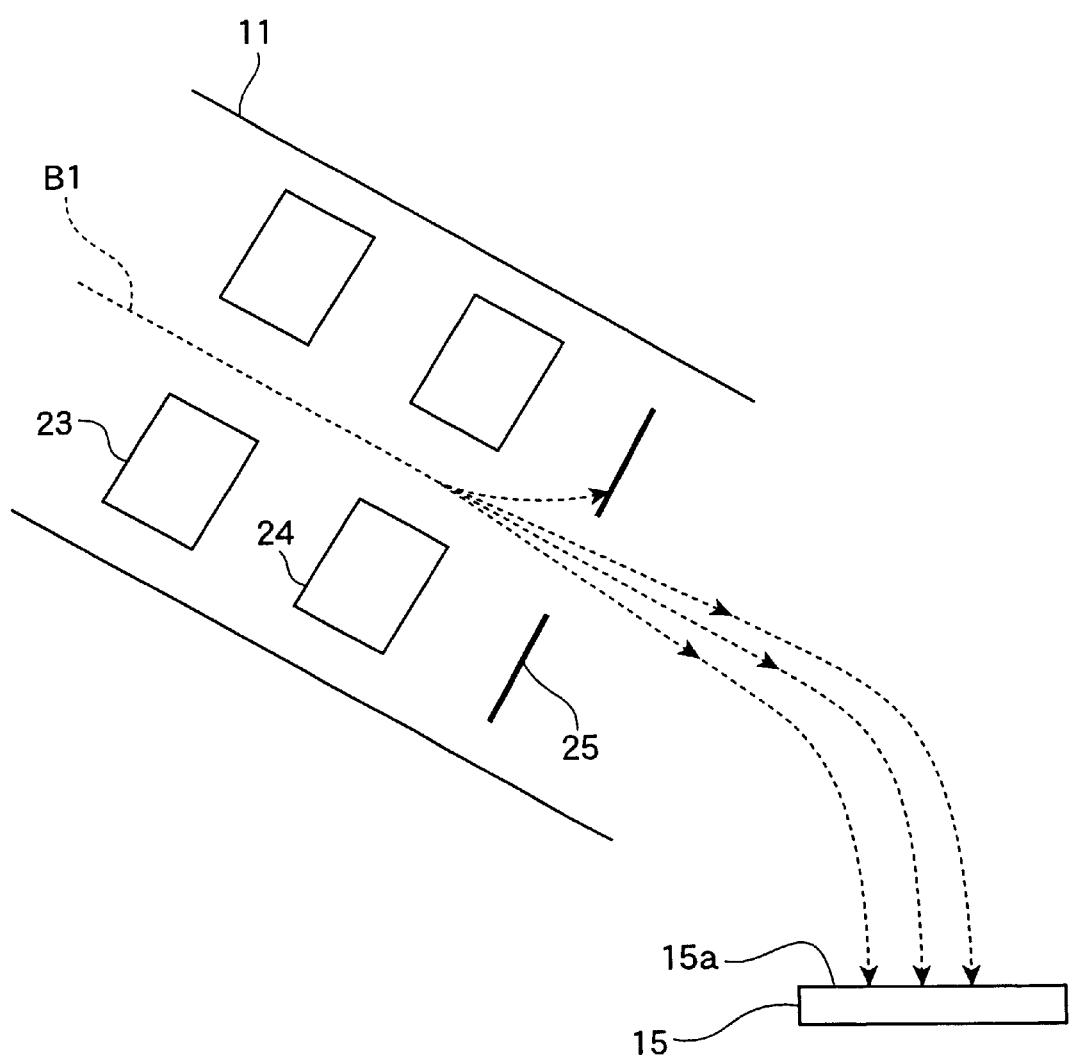
FIG. 6 is a drawing explaining the deflection of the primary beam by the primary polarizer 24.

The XY position of the irradiated region 21A (see FIG. 5) of the primary beam B1 can be moved on the specimen surface 15a by controlling the voltage applied to the primary polarizer 24 and deviating the trajectory of the primary beam B1 (see FIG. 6).

It is also possible to greatly deviate the trajectory of the primary beam B1 by controlling the voltage applied to the primary polarizer 24 and preventing the primary beam B1 from passing the opening section of the aperture 25. The voltage applied to the primary polarizer 24 in this event is called the "blanking voltage."

When the specimen 15 is irradiated with the primary beam B1, the secondary beam B2 comprising at least 1 kind of the secondary electron, reflected electron, or backscattered electron is generated from the specimen in the irradiated region 21A. This secondary beam B2 has the two-dimensional image information of the irradiated region 21A. Because the primary beam B1 is applied perpendicularly with respect to the specimen surface 15A as described above, the secondary beam B2 has a clear image free of shades. Now, because the retarding voltage Vr is applied to the stage 28 on which the specimen 15 is held, the electric field positive to the secondary beam B2 is formed between the specimen 15 and the electrode 31a of the cathode lens 31. Consequently, the secondary beam B2 generated from the specimen 15 is accelerated towards the cathode lens 31.

And the secondary beam B2 is subject to the focusing action by the cathode lens 31 and passes the numerical aperture 32 and at the same time goes straight as it is without being subject to polarization action of the Wien filter 33, and forms image at the opening section of the field aperture 3 via the second lens 34. In this way, it is possible to suppress the generation of the lens aberration by forming the first image of the secondary beam B2 generated from the specimen 15 by joint efforts of the cathode lens 31 and the second lens 34.

By the way, varying the electromagnetic field applied to the Wien filter 33 can select the electron (for example, secondary electron, reflected electron, or backscattered electron) with a specific energy band only from the secondary beam B2 and allow it to pass.

The secondary beam B2 that has passed the field aperture 35 repeats focusing and divergence by the third lens 36 and the fourth lens 37 located in the latter stage and forms image again on the detection surface of the detector 39 after is passes the polarizer 38. The number of image formations in this event may be one time each (a total of two times) by the third lens 36 and the fourth lens 37 or may be once as a result of cooperation with the third lens 36 and the fourth lens 37. In either case, the intermediate image of the irradiated region 21A obtained at the opening section of the field aperture 35 is enlarged and projected on the detection surface of the detector 39 via the third lens 36 and the fourth lens 37.

Furthermore, the secondary beam B2 which formed image again on the detection surface of the detector 39 is accelerated and multiplied when it passes MCP43 in the detector 39 and converted into light by the fluorescent plate 44. And the light from the fluorescent plate 44 forms image on the image pickup surface of the TDI sensor 45 via the optical relay lens 47. That is, the two-dimensional image of the irradiated region 21A enlarged and projected on the detection surface of the detector 39 is converted into the optical image in the fluorescent plate 44 and is projected on the image pick-up surface of the TDI sensor 45 via the optical relay lens 47. The image of the irradiated region 21A which is projected on the image pickup surfaces of this TDI sensor 45 is hereinafter called the "specimen image 45A."

Figure 7:
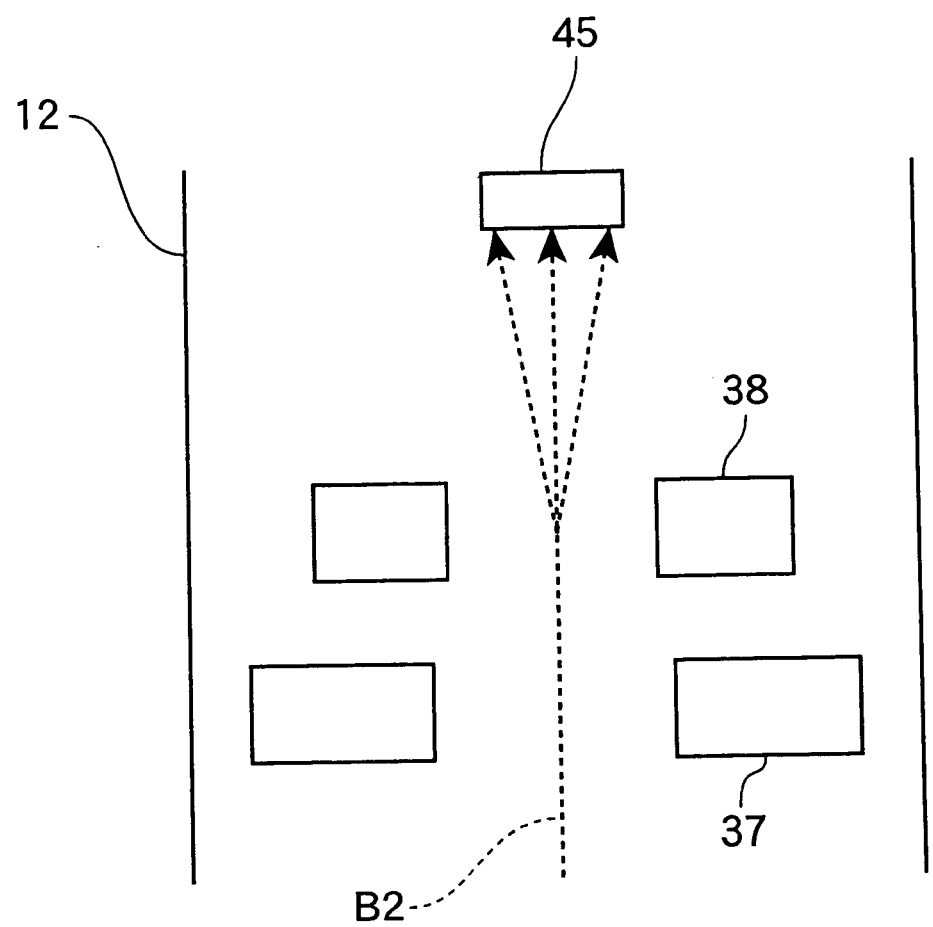
FIG. 7 is a drawing explaining the deflection of the primary beam by the secondary polarizer 38.
Figure 8A:
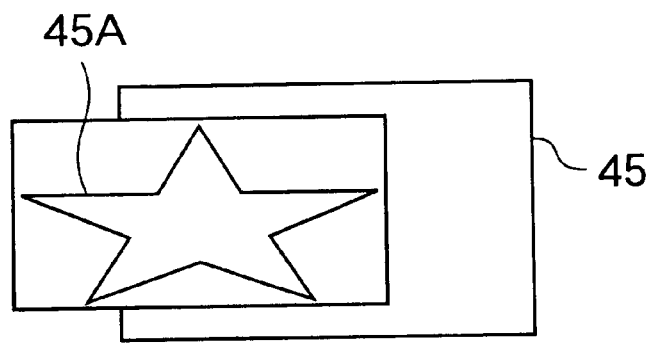
FIG. 8A is a drawing explaining the move of the specimen image 45A by the secondary polarizer 38.
Figure 8B:
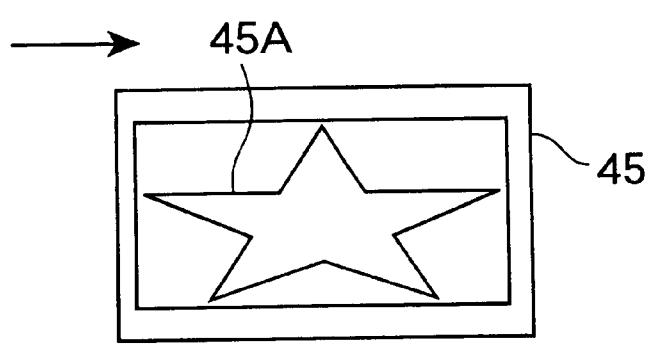
FIG. 8B is a drawing explaining the move of the specimen image 45A by the secondary polarizer 38.
Figure 8C:
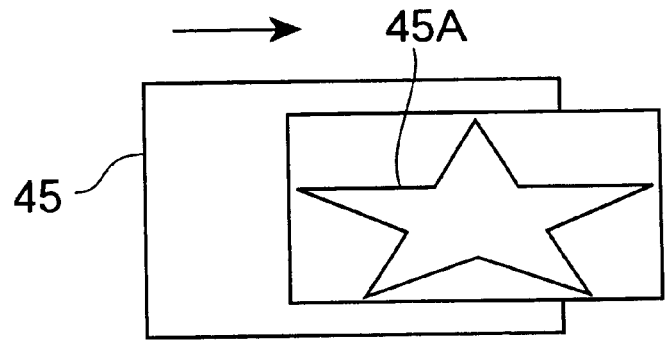
FIG. 8C is a drawing explaining the move of the specimen image 45A by the secondary polarizer 38.

The projection position of the specimen image 45A is able to be moved on the image pickup surface of the TDI sensor 45 as shown in FIGS. 8A to 8C by controlling the voltage applied to the secondary polarizer 38 and deviating (see FIG. 7) the trajectory of the secondary beam B2.

Now, the corresponding relation between the projection position of the specimen image 45A and the voltage applied to the secondary polarizer 38 is known. Consequently, in the secondary polarizer control unit 42, it is possible to project the specimen image 45A to a specified position of the image pickup surface of the TDI sensor 45 or move the specimen image 45A at a specified velocity. The move of the specimen image 45A by the secondary polarizer 38 in this way is utilized in the observation mode later discussed.

Figure 9A:
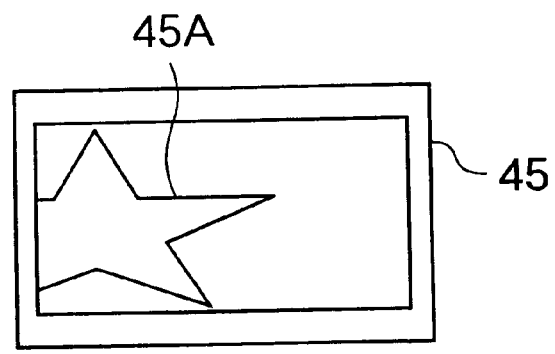
FIG. 9A is a drawing explaining the move of the specimen image 45A by the stage 28.
Figure 9B:
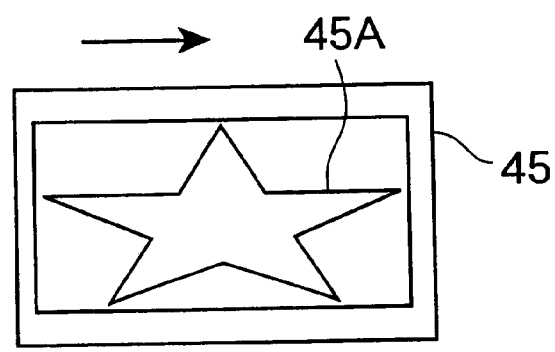
FIG. 9B is a drawing explaining the move of the specimen image 45A by the stage 28.
Figure 9C:
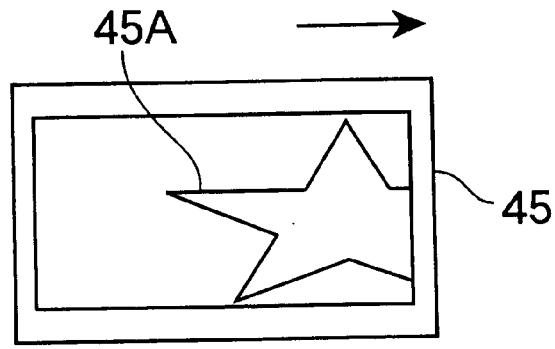
FIG. 9C is a drawing explaining the move of the specimen image 45A by the stage 28.

Furthermore, the projection position of the specimen image 45A is able to be moved on the image pickup surface of the TDI sensor 45 as shown in FIGS. 9A to 9C by varying the position of the specimen 15 with respect to the irradiated region 21A (see FIG. 5).

In this event, in the stage control unit 29, it is possible to project the specimen image 45A on the specified position of the image pickup surface of the TDI sensor 45 or move the specimen image 45A at a specified velocity by controlling the XY position and moving velocity of the stage 28. Movement of the specimen image 45A effected by such a stage 28 is utilized in an inspection mode described later.

Figure 10:
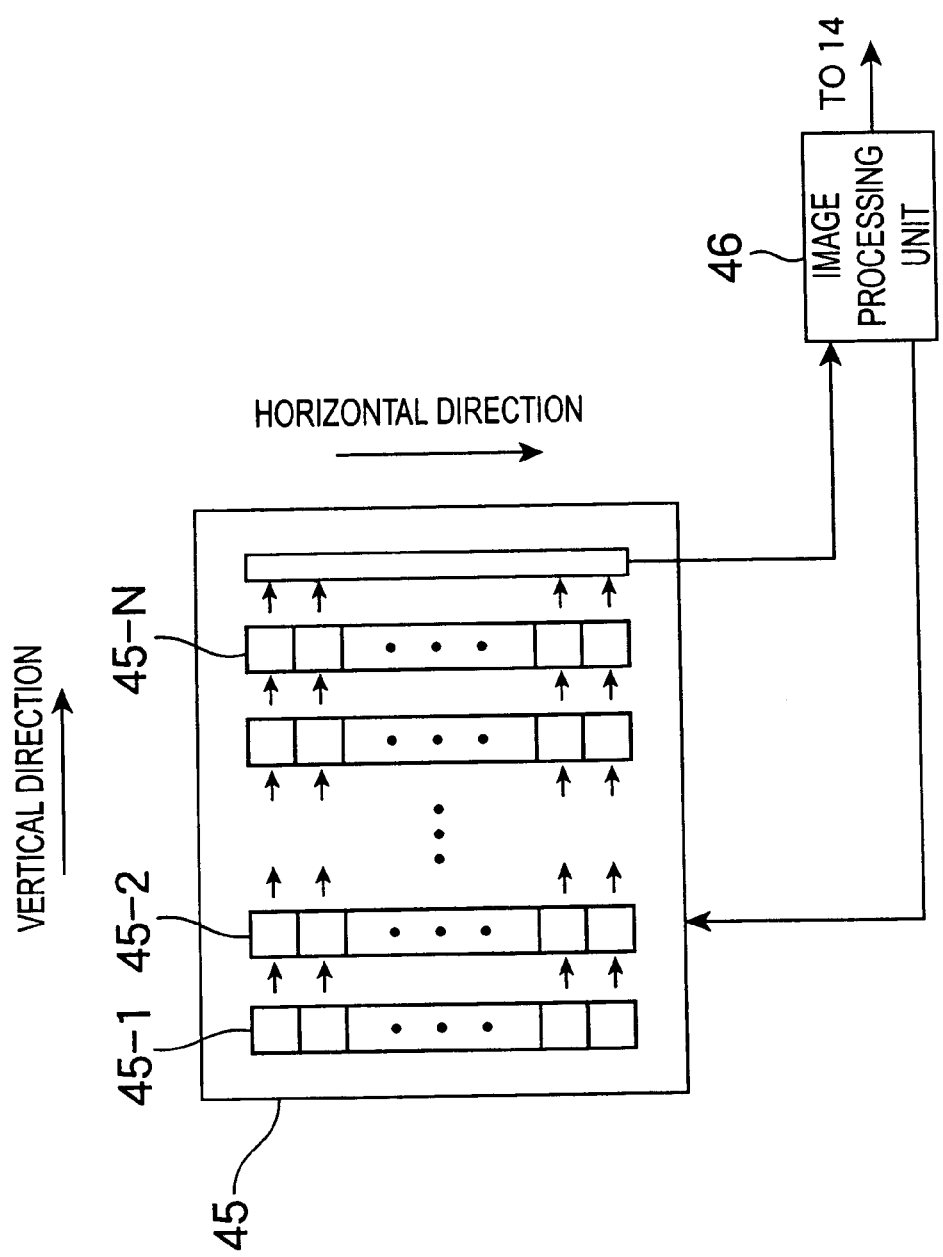
FIG. 10 is a drawing explaining the TDI sensor 45.

Now, the specimen image 45A projected on the image pickup surface of the TDI sensor 45 is converted to signal charge of a plurality of each light-receiving pixel (see FIG. 10) that compose the image pickup surface of the TDI sensor 45. And the signal charge of each light receiving pixel is transferred successively in the vertical direction and in the horizontal direction in accordance with the driving pulse imputed from the image processing unit 46, and is outputted to the image processing unit 46.

The rate when the signal charge is horizontally transferred or vertically transferred is set to different values in the observation mode and in the inspection mode later discussed, respectively, as shown in Table 2.

TABLE 2

|  | OBSERVATION MODE | INSPECTION MODE |
|---|---|---|
| EFFECTIVE DATA TRANSFER RATE (HZ/PIX) | 2.29E+07 | 9.15E+07 |
| LINE RATE (HZ/LINE | 11175 | 44700 |

The vertical transfer of signal charge takes place for every horizontal line 45-1 to 45-N in synchronism with the move of the specimen image 45A (FIGS. 8A–8C or FIGS. 9A–9C). Consequently, the signal charges accumulated in each of the horizontal lines 45-1 to 45-N of the TDI sensor 45 are integrated every time the signal charge is transferred in the horizontal line adjacent to the vertical direction.

The image processing unit 46 A/D converts the output signal from the TDI sensor 45, stores in the VRAM inside, and generates and outputs the image information of the specimen 15 to the host computer 14. The host computer 14 displays the image on CRT 16 in conformity to the image information outputted from the image processing unit 46.

Now, the actions of the EB inspection apparatus 10 configured as above will be described. For the actions of the EB inspection apparatus, there are an observation mode for acquiring the image of the specimen 15 with the stage 28 stopped and an inspection mode for acquiring the image of the specimen 15 at a high speed with the stage moved. In either mode, in the EB inspection apparatus 10, the size at the specimen 15 corresponding to one light receiving pixel of the TDI sensor 45 is adjusted to become 0.1 $\mu$m.

First of all, the observation mode will be described.

In the observation mode, the range control unit 29 drives the stage 28 in XY directions and positions the region desired to observe (for example, region including a defect portion) in the specimen 15 to the inside of the irradiated region 21A of the primary beam B1. After positioning, the stage 28 is stopped. The electron gun control unit 22 controls the acceleration voltage Vac of the electron gun 21 and sets the irradiated current volume Ib of the primary beam B1 to 62.5 nA (see Table 1).

Furthermore, the image processing unit 46 supplies the driving pulse to the TDI sensor 45 in conformity to the observation timing signal from the host computer 14. As a result, the signal charge of the specimen image 45A converted by each light receiving pixel of the TDI sensor 45 is transferred successively at an effective data transfer rate of 2.29E+07 Hz/pix and line rate of 11175 Hz/line (see Table 2).

On the other hand, the secondary polarizer control unit 42 controls the voltage applied to the secondary polarizer 38 in conformity to the observation timing signal from the host computer 14. As a result, the specimen image 45A projected on the image pick-up surface of the TDI sensor 45 moves in the vertical direction at a specified velocity according to the line rate (11175 Hz/line) (FIGS. 8A–8C). As described above, by synchronizing the move of the specimen image 45A in the TDI sensor 45 with the vertical transfer of the signal charge, the signal charge of the specimen image 45A is integrated and outputted to the image processing unit 46 (specimen image). According to this observation mode, the image of the region desired to observe (for example, a region including a defect portion) in the specimen 15 is able to be constantly displayed on CRT 16. Furthermore, according to this observation mode, by picking up the image of the specified test pattern, various adjustments are able to be carried out, including focus adjustment of the primary optical system 23 and secondary optical system (31–37), aberration adjustment, brightness adjustment in the detector 39, etc.

Now, the description will be made on the action for acquiring the specimen image in the inspection mode. In the inspection mode, the electron gun control unit 22 controls the acceleration voltage Vac of the electron gun 21 and sets the irradiated current volume Ib of the primary beam B1 to 250 nA (see Table 1). The image processing unit 46 supplies the driving pulse to the TDI sensor 45 in conformity to the inspection timing signal form the host computer 14. As a result, the signal charge of the specimen image 45A converted by each light receiving pixel of the TDI sensor 45 is transferred successively at an effective data transfer rate of 9.15E+07 Hz/pix and line rate of 44700 Hz/line (see Table 2).

On the other hand, the stage control unit 29 moves the stage 28 at a high speed in conformity to the inspection timing signal from the host computer 14. As a result, the specimen image 45A projected on the image pick-up surface of the TDI sensor 45 moves in the vertical direction at a specified velocity according to the line rate (44700 Hz/line) (FIGS. 9A–9C). As described above, by synchronizing the move of the specimen image 45A in the TDI sensor 45 with the vertical transfer of the signal charge, the signal charge of the specimen image 45A is integrated and outputted to the image processing unit 46 (specimen image).

According to this inspection mode, because the image pickup action is executed while the stage 28 is being moved at a high speed, it is possible to take in the specimen image continuously and in a short time from a comparatively wide range or the whole of the specimen surface 15a. Because the stage 28 is moved at a high speed, thee is a possibility to cause minor displacement (1 $\mu$m or less) of the specimen image 45A arising from speed variation or mechanical vibration of the stage 28, but the displacement of the specimen image 45A is able to be compensated for by supplying the position compensation voltage to the secondary polarizer 36. When the acquisition of the specimen image in the inspection mode completes, the host computer 14 can specify the defect position of the specimen 15 by executing template matching, etc. for the image information.

Next discussion will be made on the features of the EB inspection apparatus 10 according to the present embodiment.

In the inspection mode of the EB inspection apparatus 10 mentioned above, in order to increase the inspection speed, the moving velocity of the stage 28 was accelerated and at the same time the transfer rate (see Table 2) of the signal charge in the TDI sensor 45 was also set to a faster value. And the irradiation current volume IB (see Table 1) of the primary beam B1 was set to a stronger value as much as the moving velocity and the transfer rate were increased. That is, the inspection mode above is to carry out a high-speed inspection by continuously irradiation the specimen surface 15a with a large-current beam, while the stage is being moved continuously and at a high velocity. Consequently, if the stage 28 should stop or the moving velocity should decrease for some reason during the high-speed inspection, the large current beam is continuously applied to the same place or the vicinity of the specimen surface, and the dosage rapidly increase (see Eqs. (1) and (2) above).

However, there is a limit to the acceptable dosage for the specimen 15, and if the primary beam B1 is irradiated exceeding this allowable range of dosage, contamination or charge-up are caused in the specimen 15 or for the worst, the specimen 15 may be destroyed. Therefore, the EB inspection apparatus 10 according to the present embodiment has a specimen protection mechanism incorporated to protect the specimen 15.

Figure 11A:
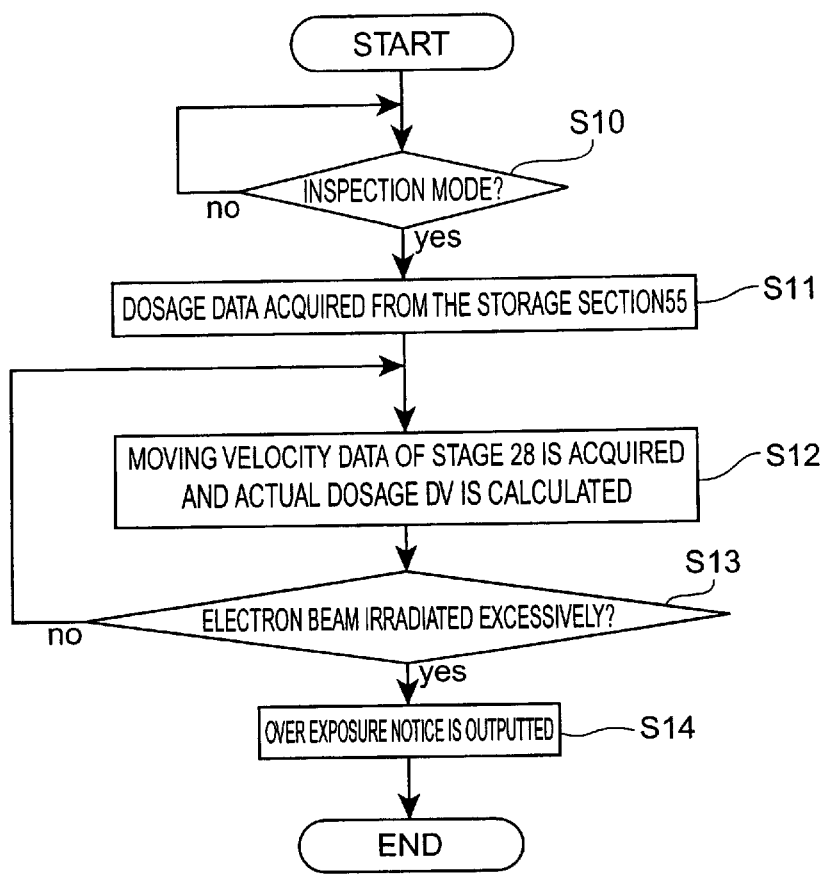
FIG. 11A is a flow chart explaining the specimen protection mechanism.
Figure 11B:
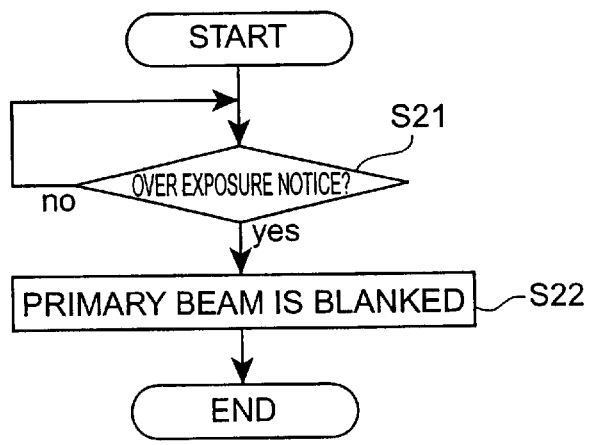
FIG. 11B is a flow chart explaining the specimen protection mechanism.

Referring now to flow charts shown in FIGS. 11A and 11B, the action of the specimen protection mechanism 50 incorporated in the EB inspection apparatus 10 will be described.

The host computer 14 acquires the predetermined dosage data for the specimen 15 to be inspected when it receives a command of inspection mode to be entered from the outside (S10), acquires the predetermined dosage data from the stored section 55 for the specimen 15 (S11), and temporarily accumulated in the over exposure detection section 53.

Then, the host computer 14 acquires the signal concerning the moving velocity V of the stage 28 entered from the stage control unit 29 to the control section 52 via the interface section 51. The control section 52 transmits the entered signal to the dosage measurement section 54. The dosage measurement section 54 calculates the dosage Dv of the electron beam actually applied to the specimen 15 (S12) in conformity to the transmitted moving speed V, the irradiated current volume Ib of the primary beam B1, and the area S of the irradiated region 21A (see Eq. (2)).

Next, the over exposure detection section 53 of the host computer 14 judges whether the specimen is excessively irradiated with the electron beam by comparing the dosage data acquired from the storage section 55 with the actual dosage Dv calculated by the dosage measuring section 54 (S13). And if the dosage Dv measured by the dosage measuring section 54 is greater than the dosage stored in the storage section 55, the over exposure of electron beam is detected. And when the over exposure of electron beam is detected, the control section 52 of the host computer 14 outputs a notice of over exposure of the electron beam to the primary polarizer control unit 27 (S14). On the other hand, if the actual dosage Dv is smaller than the dosage acquired from the storage section 55, the host computer returns to the stage where the signal concerning the moving velocity V of the stage 28 is acquired (S12). Consequently, as long as the actual dosage Dv is smaller than the allowable range data, the specimen image acquiring action continuously takes place in the inspection mode mentioned above.

When the primary polarizer control unit 27 receives the notice of over exposure of electron beams from the host computer 14 (S21), it applies blanking voltage to the primary polarizer 24 and greatly polarizes the trajectory of the primary beam B1 as shown in FIG. 6, and prevents electron beams from passing the opening section of the aperture 25 (S22). As a result, the specimen 15 is not irradiated with the large-current primary beam B1. Consequently, the worst condition such as generation of contamination or charge-up in the specimen 15 or destruction of the specimen 15 can be avoided.

Figure 12:
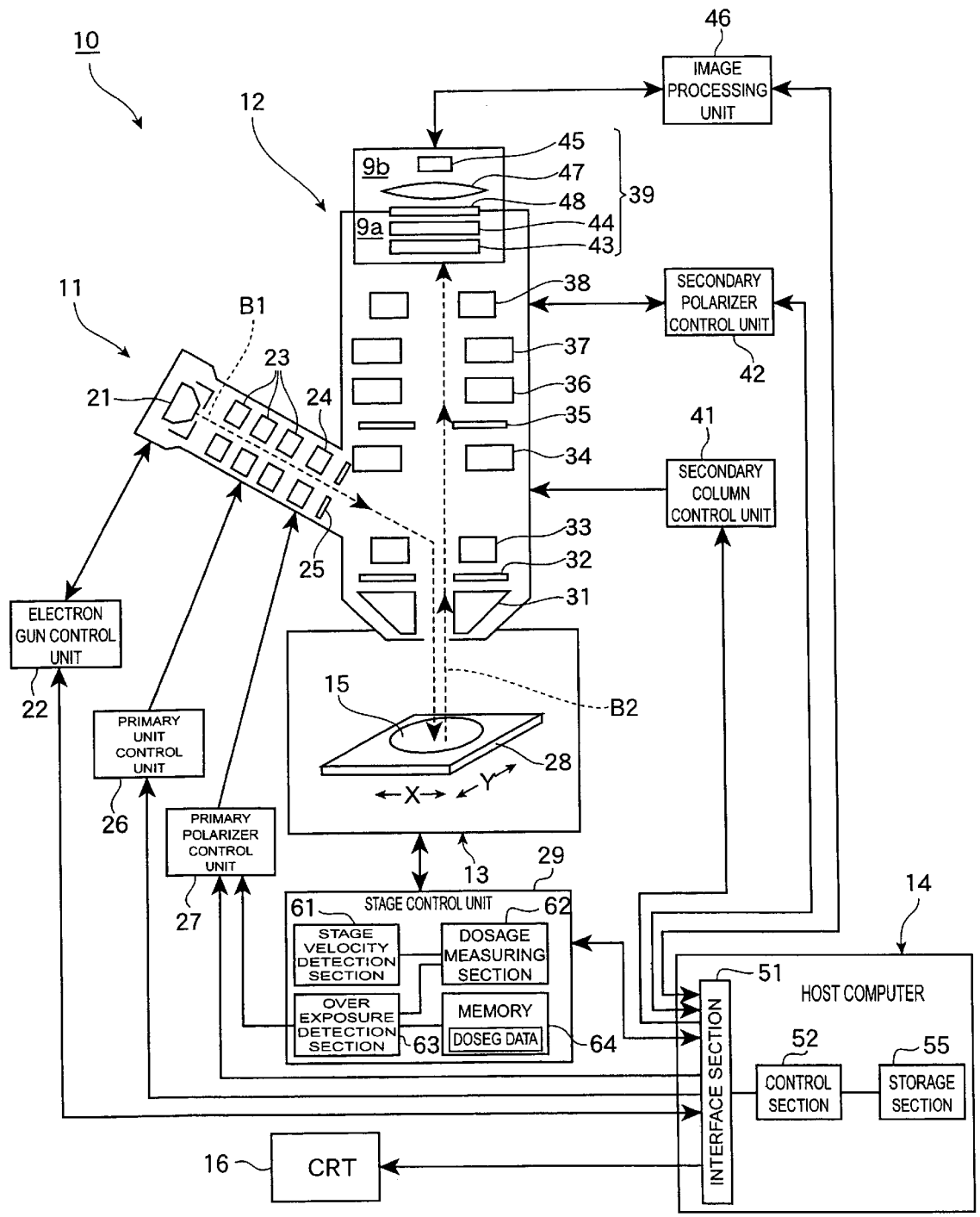
FIG. 12 is a drawing showing the other example of the EB inspection apparatus according to the present embodiment.

In the above-mentioned embodiment, the host computer is configured to contain the dosage measuring section 54 and the over exposure detection section 53, but a shown in FIG. 12, the stage control unit may be configured to contain the dosage measuring section 62 and the over exposure detection section 63. And the dosage data predetermined by the specimen to be inspected is acquired from the host computer 14 in advance and developed in the memory 64. In addition, the over exposure detection section 63 is connected in series to the primary polarizer control unit 27. In this kind of configuration, the over exposure of electron beams is able to be quickly detected by comparing the dosage Dv of the electron beam measured by the dosage measuring section 62 with the dosage data developed in the memory 64, and if over exposure of electron beams is detected, it is notified to the primary polarizer control unit 27 and blanking of electron beams is able to be carried out quickly.

In the above-mentioned embodiment, a description was made on an example to outputting the notice of over exposure from the host computer 14 to the primary polarizer control unit 27 and blanking the primary beam B1 by the primary polarizer 24, but the present invention shall now be limited to this configuration. For example, the notice of over exposure of electron beams from the host computer 14 is outputted to the electron gun control unit 22 and the electron discharge of the electron gun 21 may be stopped by turning off the power supply of he electron gun 21. If a driving mechanism that moves the position of the aperture 25 in the surface intersecting the trajectory of the primary beam B1 is disposed, the notice of the over exposure of electron beams is outputted to this driving mechanism to move the aperture 25, and the trajectory of the primary beam B1 may be intercepted by the plate section (place other than the opening section) to carry out blanking of the primary beam B1. Needless to say, a shutter mechanism dedicated for intercepting the trajectory of the primary beam B1 may be installed. If a polarizer other than the primary polarizer 24 or apertures other than the aperture 25 is located in the trajectory of the primary beam B1, blanking control similar to the above-mentioned may be carried out using these other a polarizer and apertures.

Furthermore, in the above-mentioned embodiment, discussion was made on an example in which the primary beam B1 is completely intercepted by the notice of over exposure of electron beams from the host computer 14 and the specimen 15 is prevented from being irradiated with the primary beam B1, but the irradiation of the primary beam B1 may be controlled and the current density of the primary beam B1 (=irradiating current volume Ib/(area S of the irradiated region 21A)) may be reduced to prevent rapid increase of the dosage.

Specifically, there is a method for using a primary polarizer, deflecting the trajectory of the primary beam B1 at high velocity and in a wide range, and to prevent the irradiated region 21A from staying in the same place on the specimen surface 15a. In addition, a method to increase the area S of the irradiated region 21A by expanding the cross section of the primary beam B1 by the use of the primary optical system 23 can lower the current density of the primary beam B1 and can prevent rapid increase of the dosage (corresponds to clam 3). Furthermore, similarly, an increase of the dosage is able to be prevented by a method for controlling the acceleration voltage Vac of the electron gun and lower the outgoing current volume Ia of the primary beam B1.

Figure 13:
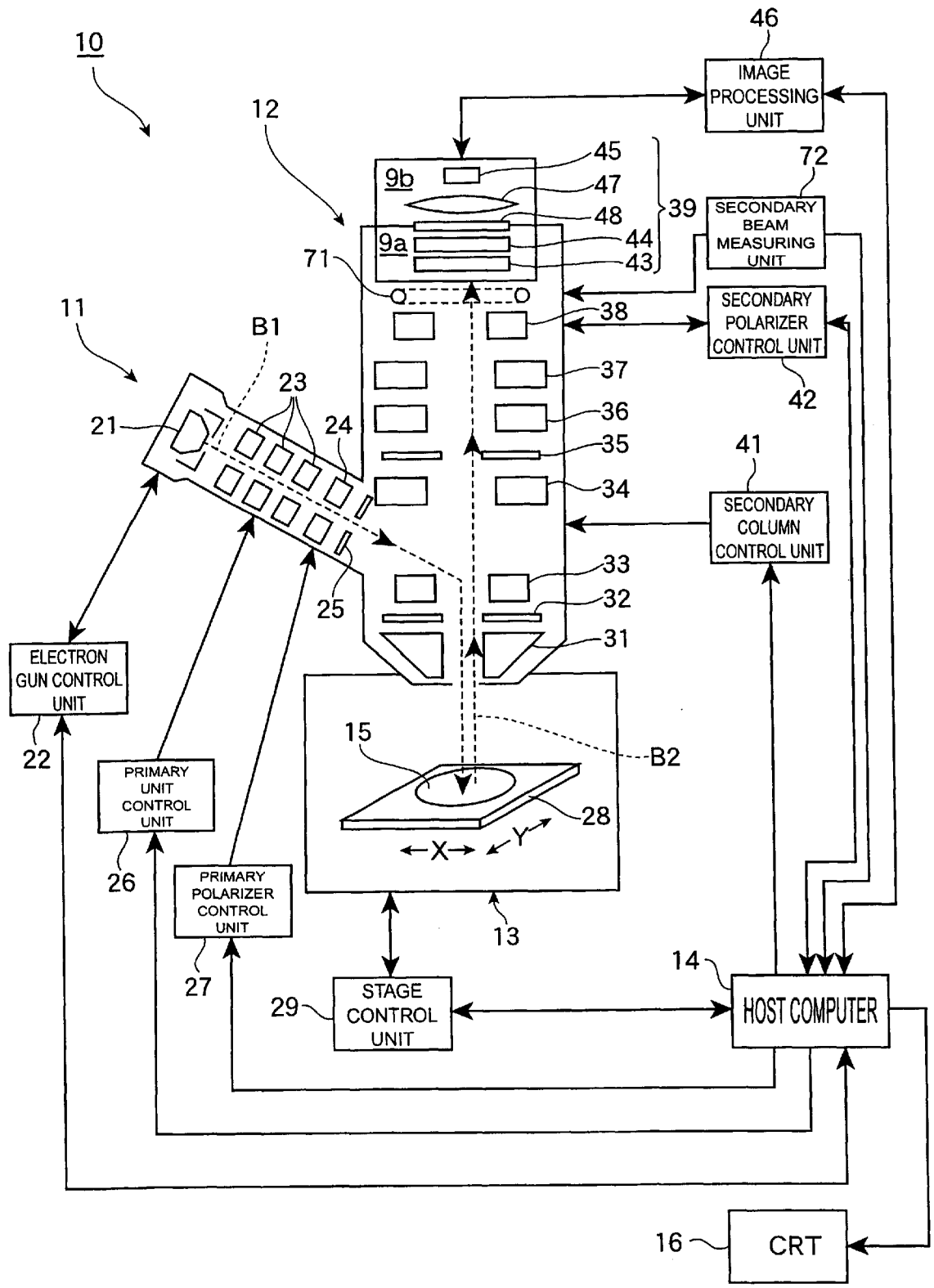
FIG. 13 is a drawing showing another example of the EB inspection apparatus according to the present embodiment.

In the above-mentioned embodiment, an example for calculating the actual dosage Dv was discussed in conformity to the moving speed of the stage 28 detected by the stage control unit 29, but the present invention shall not be limited to this configuration. For example, because as the dosage of the specimen 15 increases, the amount of the secondary beam B2 generated from the specimen 15 increases, the actual dosage Dv is also be able to be detected by detecting the generation volume of secondary beam B2 and making the best of the corresponding relation between the secondary beam B2 generation volume and the dosage of specimen 15 (corresponds to claim 5). By the way, the generation volume of secondary beam B2 can be detected by disposing the detection coil around the trajectory of the secondary beam B2 as shown in FIG. 13 and connecting to the secondary beam B2 measuring unit for measuring the volume of the secondary beam B2 by the current outputted from the detection coil. Because to the fluorescent plate 44 composing the detector 39, a specified voltage is applied and current flows by collisions of the secondary beam B2, it is possible to detect the generation volume of the secondary beam B2 in conformity to the current that flows this fluorescent plate 44.

In addition, because as the dosage of the specimen 15 increases, the specimen image becomes brighter and the contrast ratio lowers, it is also possible to detect the actual dosage Dv by detecting the contrast ratio of the specimen image and at the same time by utilizing the corresponding relation between this contrast ratio and the material 15 (corresponds to claim 9). By the way, the detection of the contrast ratio of the specimen image is enabled by comparing the mean value of the concentration of each light receiving pixel stored in memory in the image processing unit 42 with the threshold value of the predetermined concentration.

In the above-mentioned embodiment, the description was made on an example in which the allowable range data of the dosage of the specimen 15 is stored in the storage section 55 of the host computer 14 and the allowable range data is compared with the actual dosage Dv to judge whether the over exposure of electron beams has occurred or not in the inspection mode, but the present invention shall not be limited to this configuration. For example, the allowable range data of the moving velocity of the stage 28 is calculated in advance in conformity to the allowable range data of the dosage of the specimen 15 and this allowable range data of the moving velocity may be stored in the storage section 55 of the host computer 14. In such event, the over exposure of the electron beam in the inspection mode is able to be detected by comparing the allowable range data of the moving velocity of the stage 28 with the actual moving velocity of the stage 28 (corresponds to claim 6). Similarly, the allowable range data of the secondary beam B2 is calculated in advance in conformity to the allowable range data of the dosage of the specimen 15, and this allowable range data of the generation volume of the secondary beam B2 may be stored in the storage section 55 of the host computer 14. In such event, the over exposure of the electron beam in the inspection mode is able to be detected by comparing the allowable range data of the generation volume of the secondary beam B2 with the actual generation volume of the secondary beam B2 (corresponds to claim 7). Furthermore, the allowable range data of the contrast ratio of image information is calculated in advance in conformity to the allowable range data of the dosage of the specimen 15, and this allowable range data of the contrast ratio of image information may be stored in the storage section 55 of the host computer 14. In such event, the over exposure of the electron beam in the inspection mode is able to be detected by comparing the allowable range data of the contrast ratio of image information with the actual contrast ratio of image information (corresponds to claim 10).

In the above-mentioned embodiment, discussion was made on an example in which the primary beam B1 is not polarized while the specimen image is being acquired in the inspection mode (irradiated region 21A is not moved), but the present invention is applicable even when the specimen image is acquired while the primary beam B1 is polarized (irradiated region 21A is being moved). Furthermore, in the above-mentioned embodiment, an inspection apparatus using the primary beam B1 shaped in a plane form was taken for an example, but the present invention is able to be applied when inspection is carried out using the primary beam B1 squeezed in the spot form.

That is, the present invention can be applied to any of the configurations including SEM, in which the specimen image is acquired while the primary beam B1 is moved relative to the specimen. In the above-mentioned embodiment, an example for joining the electron optical system of the primary column 11 (primary optical system 23) to the electron optical system of the secondary column (second lens, etc.) with the Wien filter 33, but the inspection method of the present invention is able to applied to the case in which they are configured separately.

Because according to the electron beam apparatus related to the present invention, when the specimen is irradiated with the electron beam while the specimen and the electron beam are relatively moved, the rapid increase of the dosage caused by the stop of the relative move or decreased speed can be prevented and the specimen can be protected, as described above, the reliability to the high-speed processing (in particular, high-speed inspection) using the large-current beam can be improved.

From the invention thus described, it will be obvious that the invention may be varied in many ways. Such variations are not to be regarded as a departure from the spirit and scope of the invention, and all such modifications as would be obvious to one skilled in the art are intended for inclusion within the scope of the following claims.

What is claimed is:

1. An electron beam apparatus for irradiating a specimen with an electron beam, comprising:

electron beam outputting means for outputting the electron beam, measuring means for measuring a dosage of the electron beam irradiated per unit area of the specimen, a storage section for storing a predetermined dosage per unit area for the specimen, detection means for detecting over exposure of the electron beam when the dosage per unit area measured by the measuring means is greater than the dosage per unit area stored in the storage section, control means for controlling the electron beam outputting means to reduce the dosage per unit area of the electron beam lower than the dosage per unit area stored in the storage section, when the over exposure of the electron beam is detected by the detection means, a stage on which the specimen is placed, and moving means for moving the stage, wherein the measuring means measures the dosage per unit area in accordance with an output current volume of the electron beam and a moving speed of the stage moved by the moving means.

2. The electron beam apparatus according to claim 1, wherein the control means controls the electron beam outputting means to reduce the dosage per unit area of the electron beam lower than the dosage per unit area stored in the storage section, when the over exposure of the electron beam is detected over a specified time.

3. The electron beam apparatus according to claim 1, wherein the control means controls the electron beam outputting means in such a manner to make the dosage per unit area of the electron beam applied to the specimen smaller than the dosage per unit area stored in the storage section by expanding an irradiation range of the electron beam.

4. The electron beam apparatus according to claim 1, wherein the dosage per unit area is able to be measured in accordance with a secondary beam volume generated from the specimen.

5. An inspection apparatus, comprising:

the electron beam apparatus according to claim 1, and image acquisition means for acquiring image information of the specimen in conformity to a secondary beam generation from the specimen.

6. The inspection apparatus according to claim 5, wherein the measuring means measures the dosage on the basis of the output current volume of the electron beam and a contrast ratio of the image information acquired by the image acquisition means.

7. An electron beam apparatus, comprising:

electron beam output means for outputting an electron beam, a stage irradiated with the electron beam output by the electron beam output means, moving means for moving the stage, a storage section for storing a stage moving speed predetermined in accordance with the specimen and an output current volume of the electron beam, detection means for detecting over exposure of the electron beam when a moving speed of the stage moved by the moving means is smaller than the stage moving speed stored in the storage section, and control means for controlling the electron beam output means to prevent the stage from being irradiated with the electron beam when the over exposure of the electron beam is detected by the detection means.

8. An inspection apparatus for inspecting a specimen by irradiating the specimen with an electron beam, comprising:

electron beam outputting means for outputting the electron beam and irradiating the specimen with the electron beam, image acquisition means for acquiring image information of the specimen based on a secondary beam generated from the specimen, a storage section for storing a contrast ratio predetermined on the basis of the specimen and an output current volume of the electron beam, detection means for detecting over exposure of the electron beam when the contrast ratio of the image information acquired by the image acquisition means is greater than the contrast ratio stored in the storage section, and control means for controlling the electron beam outputting means to prevent the electron beam from being applied to the specimen.

9. An inspection method for inspecting a specimen by irradiating the specimen with an electron beam, comprising:

outputting the electron beam to irradiate the specimen with the electron beam, acquiring image information of the specimen based on a secondary beam generated from the specimen, moving a stage on which the specimen is placed, detecting over exposure of the electron beam when a moving speed of the stage is smaller than a stage moving speed predetermined in accordance with the specimen and an output current volume of the electron beam, and controlling the electron beam to prevent the stage from being irradiated with the electron beam when the over exposure of the electron beam is detected.

10. An electron beam apparatus for irradiating a specimen with an electron beam, comprising:

an electron beam source that outputs the electron beam, a measuring system that measures a dosage of the electron beam irradiated per unit area of the specimen, a memory that stores a predetermined dosage per unit area for the specimen, a stage on which the specimen is placed, a drive that moves the stage, and a controller that determines that an over exposure of the electron beam exists when the dosage per unit area measured by the measuring system is greater than the dosage per unit area stored in the memory, and the controls the electron beam source to reduce the dosage per unit area of the electron beam lower than the dosage per unit area stored in the memory, when the over exposure of the electron beam is determined to exist, wherein the measuring system measures the dosage per unit area in accordance with an output current volume of the electron beam and a moving speed of the stage moved by the drive.

11. The electron beam apparatus according to claim 10, wherein the controller controls the electron beam source to reduce the dosage per unit area of the electron beam lower than the dosage per unit area stored in the memory, when the over exposure of the electron beam is determined to exist over a specified time.

12. The electron beam apparatus according to claim 10, wherein the controller controls the electron beam source in such a manner to make the dosage per unit area of the electron beam applied to the specimen smaller than the dosage per unit area stored in the memory by expanding an irradiation range of the electron beam.

13. The electron beam apparatus according to claim 10, wherein the dosage per unit area is measured by the measuring system in accordance with a secondary beam volume generated from the specimen.

14. An inspection apparatus, comprising:

the electron beam apparatus according to claim 10, and an image processor that acquires image information of the specimen in conformity to a secondary beam generated from the specimen.

15. The inspection apparatus according to claim 14, wherein the measuring system measures the dosage on the basis of the output current volume of the electron beam and a contrast ratio of the image information acquired by the image processor.

16. An electron beam apparatus, comprising:

an electron beam source that outputs an electron beam, a stage irradiated with the electron beam output by the electron beam source, a drive that moves the stage, a memory that stores a stage moving speed predetermined in accordance with the specimen and an output current volume of the electron beam, and a controller that determines that over exposure of the electron beam exists when a moving speed of the stage moved by the drive is smaller than the stage moving speed stored in the memory, and that controls the electron beam source to prevent the stage from being irradiated with the electron beam when the over exposure of the electron beam is determined to exist.

17. An inspection apparatus for inspection a specimen by irradiating the specimen with an electron beam, comprising:

an electron beam source that outputs the electron beam and irradiates the specimen with the electron beam, an image processor that acquires image information of the specimen based on a secondary beam generated from the specimen, a memory that stores a contrast ratio predetermined on the basis of the specimen and an output current volume of the electron beam, and a controller that determines that over exposure of the electron beam exists when the contrast ratio of the image information acquired by the image processor is greater than the contrast ratio stored in the memory, and controls the electron beam source to prevent the electron beam from being applied to the specimen.

* * * * *